United States Patent [19]

Hoegerle et al.

[11] 4,082,535
[45] Apr. 4, 1978

[54] PYRIMIDINE DERIVATIVES

[75] Inventors: Karl Hoegerle, Basel; Dagmar Berrer, Riehen, both of Switzerland

[73] Assignee: Ciba-Geigy Corporation, Ardsley, N.Y.

[21] Appl. No.: 701,322

[22] Filed: Jun. 30, 1976

[30] Foreign Application Priority Data

Jul. 7, 1975  Switzerland .................. 8836/75

[51] Int. Cl.² .................. A01N 9/22; C07D 239/48
[52] U.S. Cl. .................. 71/92; 260/256.4 C; 260/256.4 N; 260/256.5 R
[58] Field of Search .................. 260/256.4 N, 256.4 C, 260/256.5 R; 71/92

[56] References Cited

U.S. PATENT DOCUMENTS 3,451,802  6/1969  Neighbors et al. .................. 71/93
3,845,055  10/1974  Hoegerle et al. .................. 260/256.4 N
3,948,914  4/1976  Fischer .................. 260/256.4 N Primary Examiner—Paul M. Coughlan, Jr.
Attorney, Agent, or Firm—Frederick H. Rabin

[57] ABSTRACT

This invention relates to new pyrimidine derivatives with herbicidal activity corresponding to formula I

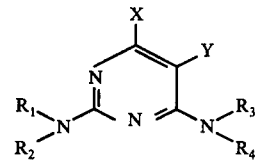

wherein X is halogen, lower alkoxy or lower alkylthio
Y is hydrogen or halogen and

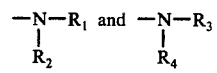

are aliphatic amino radicals, one or both of which contain the cyclopropyl ring. A process for their manufacture is given. Herbicidal compositions which contain these new pyrimidine derivatives as active component and their use for the post-emergent total or selective combating of weeds are also disclosed.

10 Claims, No Drawings

PYRIMIDINE DERIVATIVES

The present invention relates to new pyrimidine derivatives, processes for their manufacture, herbicidal agents which contain these new pyrimidine derivatives as the active component, and their use for the post-emergent total or selective combating of weeds, for example for the selective combating of tropical grasses in sugar cane cultures.

The new pyrimidine derivatives correspond to the formula I and also embrace the addition salts with inorganic and organic acids.

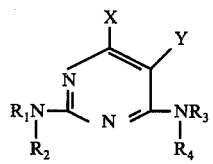  (I)

In the formula I, $R_1$ and $R_3$ independently of one another each denote a $C_1$–$C_4$-alkyl radical which can be unsubstituted or substituted by halogen, cyano, $C_1$–$C_4$-alkoxy, $C_1$–$C_4$-alkylthio, cyclopropyl or phenyl, or denote a $C_2$–$C_4$-alkenyl, $C_2$–$C_4$-alkynyl or cyclopropyl radical, $R_2$ and $R_4$ independently of one another each denote hydrogen or a $C_1$–$C_4$-alkyl radical, X denotes halogen, a $C_1$–$C_4$-alkoxy radical or a $C_1$–$C_4$-alkylthio radical and Y denotes hydrogen or halogen, with the proviso that at least one of the substituents $R_1$ and $R_3$ represents a cyclopropyl or cyclopropylalkyl group.

By addition salts there are preferably to be understood the salts of the following inorganic and organic acids: hydrogen halide acids, such as hydrochloric acid and hydrobromic acid, phosphoric acid, sulphuric acid, fluoboric acid ($HBF_4$), perchloric acid, alkylsulphuric acids such as methylsulphuric acid or ethylsulphuric acid, naphthoic acids, benzoic acid, halogenobenzoic acids, acetic acid, halogenoacetic acids such as trichloroacetic acid, aminoacetic acid, propionic acid, halogenopropionic acids, butyric acid, lactic acid, stearic acid, aliphatic dicarboxylic acids such as oxalic acid, tartaric acid and maleic acid, and aromatic sulphonic acids, such as p-toluenesulphonic acid and the like. By $C_1$–$C_4$-alkyl there are understood, in formula I, all radicals which fall under this term, namely methyl, ethyl, n- and iso-propyl, n-, iso-, sec.- and tert.-butyl. $C_2$–$C_4$-alkenyl embraces the vinyl or a butenyl radical, but preferably the allyl or methallyl radical. $C_2$–$C_4$-alkynyl are ethynyl and butynyl, but preferably propynyl or methylpropynyl radicals. The $C_1$–$C_4$-alkyl radicals can also be substituted by halogen atoms, $C_1$–$C_4$-alkoxy or alkylthio groups, the cyano group or the cyclopropyl or phenyl radical.

The pyrimidine derivatives of the formula I are new compounds. They are distinguished by a good herbicidal activity against perennial monocotyledon and dicotyledon weeds and can be used as total herbicides or as selective herbicides, for example for combating tropical grasses in sugar cane cultures by the post-emergence process.

The combating of tropical grasses, for example of the genus Cyperus (Cyperus rotundus) in sugar cane cultures by means of herbicides presents particularly great difficulties. Admittedly, Cyperus rotundus can be destroyed with 2,4-dichlorophenoxyacetic acid and its derivatives; however, the doses required for this also damage the sugar cane plants. Herbicidal active compounds from the group of the triazines do not damage the sugar cane, even in high concentrations, but also cause only little damage to, for example, Cyperus rotundus.

It has now been found, surprisingly, that pyrimidine derivatives of the formula I are able to destroy tropical grasses in sugar cane cultures, at concentrations which do not damage the sugar cane.

To destroy tropical grasses in sugar cane, amounts of 0.25 to 8 kg per hectare, preferably 1–4 kg, can be used when employing the pyrimidine derivatives of the formula I.

The treatment of the sugar cane cultures should preferably be carried out 3 to 5 weeks after planting the sugar cane, when Cyperus has emerged practically completely but has not yet flowered.

Agents according to the invention which can be used for combating tropical grasses, especially grasses of the genus Cyperus, can contain, in addition to the customary additives for agents for combating weeds, such as carriers, dispersing agents and wetting agents, also further herbicidal active compounds from the category of the phenoxyacetic acids, the phenylureas or the triazines, and the like.

The pyrimidine derivatives of the formula I are new compounds. Other pyrimidine derivatives of similar structure which in part also show a herbicidal action or some other action which influences the plant physiology have been disclosed in the following literature references: J. prakt. Chemie 115, page 292 (1927), German Offenlegungsschrift No. 2,006,145, Italian Pat. No. 662,501, French Pat. No. 2,137,933, German Offenlegungsschrift No. 2,356,644 and Noyahu Seian Gijutsu 9, 17–22 (1963).

Various methods of synthesis, which are in themselves known, are available for the manufacture of the new pyrimidine derivatives of the formula I.

A 4,6-dichloro-2-amino-pyrimidine or a 2,6-dichloro-4-amino-pyrimidine corresponding to the formula IIa and IIb

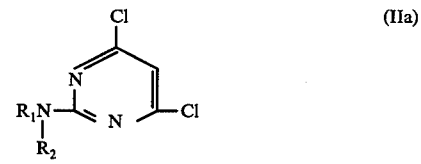  (IIa)

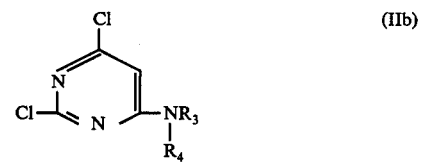  (IIb)

wherein $R_1$ to $R_4$ have the meanings given under formula I, is reacted, preferably under pressure and at elevated temperature, in an inert organic solvent and in the presence of an acid-binding agent, respectively with an amine of the formula IIIa or IIIb

  (IIIa)

$$R_1-N-H \quad \text{(IIIb)}$$
$$\phantom{R_1-N-}|$$
$$\phantom{R_1-N}R_2$$

wherein $R_1$ to $R_4$ have the meanings given under formula I.

In both cases, a 4-chloro-2,6-diamino-pyrimidine of the formula Ia

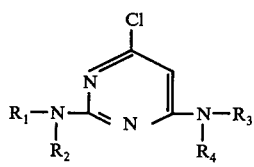

wherein $R_1$–$R_4$ have the meaning indicated under formula I, is formed.

The 4-chloro-2,6-diamino-pyrimidines thus obtained can themselves be used as the end product or can be converted into other end products by replacing the chlorine atom in the 4-position by another halogen atom in an inert organic solvent, or replacing the chlorine atom in the 4-position by an alkoxy or alkylthio radical by treatment in a $C_1$–$C_4$-alkanol or $C_1$–$C_4$-alkylthiol, or a reactive ester of such an alkanol or alkylthiol, in the presence of an acid-binding agent.

Furthermore, the hydrogen atom in the 5-position of the pyrimidine derivative can be replaced by a halogen atom by treatment with halogen or with a halogen donor in the presence of an inert solvent, preferably an alkyl halide.

The reaction of the dichloro-amino-pyrimidine with an amine of the formulae IIIa or IIIb is advantageously carried out at an elevated temperature, which can be between 50° and 200° C depending on the solvent and on the pressure used. Solvents used for this reaction are inert solvents, such as alkanols, ketones, ethers and cyclic ethers, dioxane being preferred.

The replacement of the chlorine atom in the 4-position of the pyrimidine ring by another halogen atom is advantageously carried out in a polar aprotic solvent such as dimethylformamide, dimethylsulphoxide or a halogenated or unsubstituted hydrocarbon, whilst the replacement by a $C_1$–$C_4$-alkoxy or $C_1$–$C_4$-alkylthio radical can preferably be carried out in a lower alkanol, for example propanol, in the presence of an acid-binding agent, such as a secondary or tertiary organic base or an alkali metal or alkaline earth metal hydroxide, carbonate or bicarbonate. A suitable temperature range for this replacement reaction is from 0° C to the boiling point of the solvent.

The replacement of the hydrogen atom in the 5-position of the pyrimidine ring by a halogen atom is advantageously carried out at a low temperature, between −20° C and +30° C, in a lower, optionally halogenated hydrocarbon, such as carbon tetrachloride or methylene chloride.

Some of the 2,6-dichloro-4-alkyl-, -alkenyl- or alkynyl-amino-pyrimidines or 4,6-dichloro-2-alkyl-, -alkenyl-or -alkinyl-amino-pyrimidines are known and are in some cases described in the abovementioned literature references.

Others, particularly the cyclopropylamino-dichloro-pyrimidines, had to be prepared by reaction of 2,4,6-trichloro-pyrimidine with an amine according to the formulae IIIa or IIIb. This reaction is advantageously carried out in an inert solvent, for example toluene, in the presence of an equimolar amount of an acid-binding agent, at temperatures between −30° and +30° C.

The examples which follow illustrate the preparation of some of the pyrimidine derivatives of the formula I, according to the invention; in the examples, the temperatures are given in degrees centigrade.

EXAMPLE 1

2,4-Di-cyclopropylamino-6-chloropyrimidine

A solution of 151.5 g (1 mol) of 2,4,6-trichloropyrimidine in 300 ml of acetonitrile is taken and 285 g (5 mols) of cyclopropylamine are added dropwise at 20°–30°, whilst cooling. The solution is warmed to 40° for 5 hours and to 70° for about 12 hours. The suspension is concentrated to dryness on a rotary evaporator and the residue is thoroughly stirred with 1,500 ml of methylene chloride and 1,000 ml of water for 30 minutes. The undissolved constituent is filtered off on a cloth filter. It consists of practically pure 4,6-di-cyclopropylamino-2-chloropyrimidine. The phases of the filtrate are separated and the organic phase is again extracted with water, dried and concentrated to give an oil. This is distilled under a high vacuum (boiling point 149°–51°/0.1 mm) and is then recrystallised from methanol, with addition of water. The colourless product has a melting point of 58°–60°.

EXAMPLE 2

2-Ethylamino-4-cyclopropylamino-6-chloropyrimidine

A mixture of 130.5 g (0.64 mol) of 4-cyclopropylamino-2,6-dichloropyrimidine, 576 g (6.4 mols) of ethylamine and 500 ml of ethanol is heated to the reflux temperature for 3 hours. The isomer 6-ethylamino-4-cyclopropylamino-2-chloropyrimidine which crystallises out on cooling is removed by filtration. The filtrate is concentrated to dryness on a rotary evaporator and the residue is recrystallised from methanol. 102 g of colourless crystals of melting point 86°–88° are thus obtained.

EXAMPLE 3

2-Ethylamino-4-cyclopropylamino-6-methoxy-pyramidine

A suspension of 31.8 g (0.15 mol) of 2-ethylamino-4-cyclopropylamino-6-chloropyrimidine and 30.6 g (0.17 mol) of 30 percent strength methanolic sodium methylate solution in 100 ml of methanol is heated to 100° in a bomb tube for 24 hours. When the suspension has cooled it is filtered and the filtrate is concentrated to dryness. The oily residue is taken up in methylene chloride and the solution is extracted with water, dried over sodium sulphate, filtered and evaporated. The yellow oil which remains is recrystallised twice from methanol-water to give 20 g of colourless crystals of melting point 59°–60°.

EXAMPLE 4

2-Ethylamino-4-cyclopropylamino-6-methylmercapto-pyrimidine 31.8 g (0.15 mol) of 2-ethylamino-4-cyclopropylamino-6-chloropyrimidine and 30.6 g of 30 percent strength methanolic sodium methylate solution (0.17 mol) in 25 g of methanol are first introduced into a bomb tube. 8.6 g of gaseous methylmercaptan (0.18 mol) are passed in, whilst cooling. The bomb tube is sealed and is heated to 100° for 24 hours. When the contents of the tube have cooled they are concentrated on a rotary evaporator to give an oil, the latter is taken up in methylene chloride and the solution is extracted with water. After drying over sodium sulphate, filtering and evaporating, the methylene chloride solution gives a yellow oil which crystallises slowly. When recrystallised from methanol-water, 27.3 g of colourless crystals of melting point 75°-6° are obtained.

EXAMPLE 5

2-Ethylamino-4-cyclopropylamino-5-bromo-6-chloropyrimidine

A solution of 6.4 g of bromine (0.04 mol) in 30 ml of methylene chloride is added dropwise over the course of one hour to a solution of 8.5 g (0.04 mol) of 2-ethylamino-4-cyclopropylamino-6-chloropyrimidine in 300 ml of methylene chloride, whilst cooling with ice. The solution is left to stand overnight at room temperature, 150 ml of water are then added and the mixture is brought to pH 9–10 with dilute ammonia solution. The organic phase is separated off, rinsed with water, dried over magnesium sulphate, filtered and evaporated. The evaporation residue (12 g), when recrystallised from methanol-water (1:1), gives 10.4 g of colourless crystals of melting point 100°–101°.

The pyrimidine derivatives contained in the table which follows were also prepared analogously to these examples. In this table, the symbol 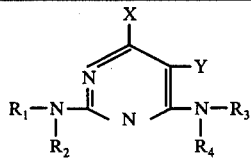 represents the cyclopropyl radical.

| No. | $R_1$ | $R_2$ | $R_3$ | $R_4$ | X | Y | Physical Constants |
|---|---|---|---|---|---|---|---|
| 1 |  | H |  | H | Cl | H | Melting point 58–60° |
| 2 | t.—$C_4H_9$ | H |  | H | Cl | H | Melting point 84–86° |
| 3 | iso—$C_3H_7$ | H |  | H | Cl | H | Melting point 87–88° |
| 4 | $CH_3$ | H |  | H | Cl | H | Melting point 109–110° |
| 5 | $C_2H_5$ | H |  | H | Cl | H | Melting Point 86–88° |
| 6 |  | H | $C_2H_5$ | H | Cl | H | Boiling point 122–125/0.001 |
| 7 |  | H | $CH_3$ | H | Cl | H | Melting point 79–80° |
| 8 |  | H | t.—$C_4H_9$ | H | Cl | H | Melting point 117–120° |
| 9 |  | H | iso—$C_3H_7$ | H | Cl | H | Oil |
| 10 |  | H |  | H | Cl | Br | Melting point 77–78° |
| 11 | $C_2H_5$ | H |  | H | Cl | Br | Melting point 99–100° |
| 12 | iso—$C_3H_7$ | H |  | H | $OCH_3$ | H | Melting point 72–74° |
| 13 | $CH_3$ | H |  | H | $OCH_3$ | H | Melting point 66–68° |
| 14 | $C_2H_5$ | H |  | H | $OCH_3$ | H | Melting point 59–60° |
| 15 | t.C—$C_4H_9$ | H |  | H | $OCH_3$ | H | Melting point 71–73° |
| 16 |  | H | $C_2H_5$ | H | OCH | H | Boiling point 107–112/0.001 |
| 17 |  | H | $CH_3$ | H | OCH | H | Melting point 55–58° |
| 18 |  | H | t.—$C_4H_9$ | H | $OCH_3$ | H | Melting point 74–76° |
| 19 |  | H | iso—$C_3H_7$ | H | $OCH_3$ | H | Boiling point 110°/0.001 |
| 20 | iso—$C_3H_7$ | H |  | H | $SCH_3$ | H | Melting point 77–79° |
| 21 | $CH_3$ | H |  | H | $SCH_3$ | H | Melting point 107–108° |
| 22 | $C_2H_5$ | H |  | H | $SCH_3$ | H | Melting point 75–76° |
| 23 | t.—$C_4H_9$ | H |  | H | $SCH_3$ | H | Boiling point 160°/0.001 |
| 24 |  | H | $C_2H_5$ | H | $SCH_3$ | H | Boilingpoint 133–134/0.001 |
| 25 |  | H | $CH_3$ | H | $SCH_3$ | H | Melting point 81–85° |
| 26 |  | H | t.—$C_4H_9$ | H | $SCH_3$ | H | Boiling point 130–133/0.001 |
| 27 |  | H | iso—$C_3H_7$ | H | $SCH_3$ | H | Boiling point 129–132/0.001 |
| 28 |  | H | $C_3H_6OCH_3$ | H | Cl | H | |

-continued

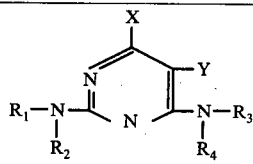

| No. | $R_1$ | $R_2$ | $R_3$ | $R_4$ | X | Y | Physical Constants |
|---|---|---|---|---|---|---|---|
| 29 | ▷— | H | —C(CH$_3$)$_2$-CN | H | Cl | H | |
| 30 | ▷— | H | ▷—CH$_2$— | H | Cl | H | |
| 31 | ▷— | H | ▷—C(CH$_3$)H— | H | Cl | H | |
| 32 | ▷— | H | C$_2$H$_5$ | C$_2$H$_5$ | Cl | H | |
| 33 | —C$_3$H$_6$OCH$_3$ | H | ▷— | H | CL | H | |
| 34 | —C(CH$_3$)$_2$-CN | H | ▷— | H | CL | H | |
| 35 | ▷—CH$_2$— | H | ▷— | H | CL | H | |
| 36 | ▷—C(CH$_3$)H | H | ▷— | H | CL | H | |
| 37 | C$_2$H$_5$ | | ▷— H | H | CL | H | |
| 38 | C$_2$H$_5$ | C$_2$H$_5$ | ▷— | H | OCH$_3$ | H | Boiling point 123°/0.35 |
| 39 | C$_2$H$_5$ | C$_2$H$_5$ | ▷— | H | SCH$_3$ | H | Boiling point 116°/0.01 |
| 40 | —C$_3$H$_6$OCH$_3$ | H | ▷— | H | SCH$_3$ | H | Melting point 71–73° |
| 41 | —C$_3$H$_6$OCH$_3$ | H | ▷— | H | OCH$_3$ | H | Melting point 107–109° |
| 42 | ▷— | H | ▷— | H | CL | CL | Melting point 74–75° |
| 43 | ▷— | H | ▷— | H | CL | F | Melting point 87–80° |
| 44 | C$_2$H$_5$ | H | ▷— | H | CL | F | Melting point 89–90° |
| 45 | ▷— | H | ▷— | H | Br | H | Melting point 82–83° |
| 46 | ▷— | H | ▷— | H | F | H | Melting point 98–99° |

The herbicidal action of the pyrimidine derivatives of the formula I was determined by the following experiments:

EXAMPLE 6

Herbicidal action when applying the active compounds after the plants have emerged (post-emergence application)

In a greenhouse, weeds which have been sown in pots, have emerged in these and are in the 4- to 6-leaf stage, are sprayed with an aqueous emulsion of the active compound (obtained from a 25% strength emulsifiable concentrate) in dosages of 0.5 to 4 kg of active substance per hectare. The plants are then kept at 24° to 26° and 45 to 60% relative atmospheric humidity. 21 days after the treatment, the experiment is evaluated. The results are rated in accordance with the 9-stage index:

9 = plants undamaged (control)
1 = plants dead
8-2 = intermediate stages of damage Composition of the emulsifiable concentrate:

25 parts of active compound, 32.5 parts of methyl ethyl ketone, 32.5 parts of water and 10 parts of a mixture of nonylphenol-polyoxyethylene and calcium dodecylsulphonate.

The evaluation of the experiment shows that compounds No. 1 and 5 of the table develop an excellent contact-herbicide action on the weeds, whilst certain crop plants, eg. maize, are spared.

EXAMPLE 7

A test plot of 1,000 m² was planted with sugar cane in February. After 20 days a mixture which contained 0.2 kg of 4-chloro-2,6-di-cyclopropylamino-pyrimidine as well as inactive carrier materials and emulsifiers was employed in a row-by-row treatment. The mixture was applied by spraying an emulsion made up with 60 liters of water. At the time of the treatment, Cyperus rotundus covered 100% of the soil surface. After 7 days all Cyperus rotundus plants had been killed, whilst no damage to the sugar cane was detectable.

A mixture containing 0.2 kg of 2-ethylamino-6-chloro-4-cyclopropylamino-pyrimidine gave the same result.

In the case of herbicidal use, the active compounds are preferably applied after the emergence of the weeds and crop plants (that is to say, post-emergent). The amounts used lie in the customary ranges of between 1 and 10 kg of active compound per hectare.

The agents according to the invention are prepared in a manner which is in itself known by intimately mixing and grinding active compounds of the formula I with suitable carriers and/or distributing agents, if appropriate with the addition of anti-foaming agents, wetting agents, dispersing agents and/or solvents which are all inert towards the active compounds. The active compounds can exist, and be used, in the following made-up forms:

Solid made-up forms: dusting agents, in particular scattering agents and granules, such as encapsulated granules, impregnated granules and homogeneous granules.

Water-dispersible active compound concentrates: wettable powders, pastes, emulsions and emulsifiable concentrates.

Liquid made-up forms: solutions.

The active compound concentrations in the agents according to the invention are from 1 to 80 percent by weight. If desired the agents can, when used, also be present at a low concentration such as about 0.05 to 1%.

Other biocidal active compounds or agents can be admixed to the agents according to the invention which have been described. Thus, in addition to the stated compounds of the general formula I, the new agents can contain, for example, insecticides, fungicides, bactericides, fungistatic agents, bacteriostatic agents, nematicides or further herbicides for broadening the spectrum of action. Preferably, light stabilisers are also added.

Emulsifiable solutions can also be used for the preparation of the aqueous use forms, for example solutions of the active compounds in fairly high-boiling organic solvents, such as xylene, to which suitable solubilising agents and/or suitable emulsifiers are admixed if desired.

Liquid or pasty concentrates can be prepared in a similar manner by mixing the active compounds with dispersing agents, organic solvents and, if appropriate, pulverised solid carriers, in suitable apparatuses, until the mixture is homogeneous; before use, these concentrates are then diluted with water.

Examples of suitable emulsifiers and dispersing agents are the alkali metal salts of sulphuric acid monoesters of long-chain aliphatic alcohols, of aliphatic-aromatic sulphonic acids or of long-chain alkoxyacetic acids, which all act as anionic agents, and the non-ionic emulsifiers and dispersing agents from the categories of the polyethylene glycol ethers of fatty alcohols or alkylphenols, the higher polycondensation products of ethylene oxide and the aliphatic-aromatic polyglycol ethers, as well as their mixtures with anionic emulsifiers.

All use forms of agents according to the invention can, if required, also contain additives to improve the rain resistance and light stability. They can furthermore contain additives which facilitate the adhesion to, and thus the penetration into, the substrate, such as, for example, vegetable, animal and mineral oils.

Dusting agents and scattering agents, the latter of which also include granules, can be prepared by mixing or conjoint grinding of the active substances with customary solid carriers. As such it is possible to use, for example: talc, diatomaceous earth, kaolin, bentonite, calcium carbonate, tricalcium phosphate and sand, but also of wood flour, cork powder and other materials of vegetable origin. However, the substances can also be absorbed on the carriers by means of a volatile solvent.

Dispersible powders are obtained by mixing, and conjoint grinding, of the active substances with solid carriers, such as, for example, chalk, kaolin, highly disperse silica and silicates, as well as with the requisite amount of wetting agent and dispersing agent.

The examples which follow illustrate the preparation of some typical embodiments of the agents according to the invention; in these, parts denote parts by weight.

GRANULES

The following materials are used to prepare 5% strength granules: 45 parts of one of the active compounds of the formula I, 0.25 part of epichlorohydrin, 0.25 part of cetyl polyglycol ether, 3.50 parts of polyethylene glycol and 91 parts of kaolin (particle size: 0.3 – 0.8 mm).

The active substance is mixed with epichlorohydrin and dissolved in 6 parts of acetone, after which the polyethylene glycol and cetyl polyglycol ether are added. The solution thus obtained is sprayed onto kaolin and is then evaporated in vacuo.

WETTABLE POWDER

The following constituents are used to prepare (a) a 70% strength and (b) a 10% strength wettable powder:
(a) 70 parts of one of the active compounds of the formula I, 5 parts of sodium dibutylnaphthylsulphonate, 3 parts of a 3:2:1 naphthalenesulphonic acids/phenolsulphonic acids/formaldehyde condensate, 10 parts of kaolin and 12 parts of Champagne chalk.
(b) 10 parts of one of the active compounds of the formula I, 3 parts of a mixture of the sodium salts of saturated fatty alcohol-sulphates, 5 parts of a naphthalenesulphonic acids/formaldehyde condensate and 82 parts of kaolin.

The stated active compound is absorbed on the appropriate carriers (kaolin and chalk) and then mixed with the other constituents, and the mixture is ground. Wettable powders of excellent wettability and suspendability are obtained. Suspensions containing 0.1 – 8% of active compound, which are suitable for combating weeds in plant cultures, can be obtained for such wettable powders by dilution with water.

PASTE

The following materials are used to prepare a 45% strength paste: 45 parts of one of the active compounds of the formula I, 5 parts of sodium aluminium silicate, 14 parts of cetyl polyglycol ether with 8 mols of ethylene oxide, 1 part of oleyl polyglycol ether with 5 mols of ethylene oxide, 2 parts of spindle oil, 10 parts of polyethylene glycol and 23 parts of water.

The active compound is intimately mixed with the additives in suitable apparatuses for this purpose, and the mixture is ground. A paste is obtained, from which suspensions of any desired concentration can be prepared by dilution with water.

EMULSION CONCENTRATE

To prepare a 25% strength emulsion concentrate, 25 parts of active compound of the formula I, 5 parts of a mixture of nonylphenol-polyoxyethylene or calcium dodecylbenzenesulphonate, 35 parts of 3,3,5-trimethyl-2-cyclohexen-1-one and 35 parts of dimethylformamide are mixed with one another. This concentrate can be diluted with water to give emulsions of suitable concentrations of, for example, 0.1 to 10%. Such emulsions can be used for combating weeds in crop plantings.

We claim:
1. A pyrimidine derivative of the formula

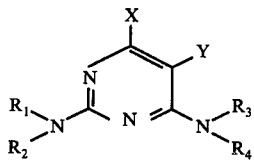

in which
- $R_1$ and $R_3$ independently denote $C_1$-$C_4$ alkyl; $C_1$-$C_4$ alkyl substituted by halogen, cyano, $C_1$-$C_4$ alkoxy, $C_1$-$C_4$ alkylthio, cyclopropyl or phenyl; $C_2$-$C_4$ alkenyl; $C_2$-$C_4$ alkynyl; or cyclopropyl,
- $R_2$ and $R_4$ independently denote hydrogen or $C_1$-$C_4$ alkyl,
- X denotes halogen; $C_1$-$C_4$ alkoxy; or $C_1$-$C_4$ alkylthio, and
- Y denotes hydrogen or halogen, with the proviso that at least one of $R_1$ and $R_3$ is cyclopropyl or cyclopropylalkyl, and an addition salt of said pyrimidine derivative with an inorganic or organic acid.

2. A pyrimidine derivative according to claim 1 in which X is chlorine and Y is hydrogen.

3. The pyrimidine derivative according to claim 2 2,4-di-cyclopropylamino-6-chloropyrimidine.

4. The pyrimidine derivative according to claim 2 2-ethylamino-4-cyclopropylamino-6-chloropyrimidine.

5. A pyrimidine derivative according to claim 1 in which X is $C_1$-$C_4$ alkoxy or $C_1$-$C_4$ alkylthio, and Y is hydrogen.

6. A herbicidal composition which comprises as active component a pyrimidine derivative according to claim 1, and a carrier.

7. The method of totally or selectively combating weeds, which comprises treating an area, where weeds have to be controlled with an effective amount of a pyrimidine derivative according to claim 1 in postemergence application.

8. The method according to claim 7 in which weeds in sugar cane cultures are selectively controlled.

9. The method according to claim 8 in which the pyrimidine derivative is 2,4-di-cyclopropylamino-6-chloropyrimidine.

10. The method according to claim 8 in which the pyrimidine is 2-ethylamino-4-cyclopropylamino-6-chloropyrimidine.

* * * * *